United States Patent [19]

Schossow

[11] 4,222,383

[45] Sep. 16, 1980

[54] SURGICAL DRAPE AND SUTURE

[76] Inventor: George W. Schossow, 2316 Lilac La., White Bear Lake, Minn. 55110

[21] Appl. No.: 931,471

[22] Filed: Aug. 7, 1978

[51] Int. Cl.$^2$ ............................................. A61B 17/08
[52] U.S. Cl. ................................. 128/335; 128/132 D
[58] Field of Search ............... 128/134 R, 134 C, 135, 128/135.5, 132 R, 132 D

[56] References Cited

U.S. PATENT DOCUMENTS

| | | | |
|---|---|---|---|
| 2,409,261 | 10/1946 | Dow | 128/335 |
| 3,698,395 | 10/1972 | Hasson | 128/335 |
| 3,971,384 | 7/1976 | Hasson | 128/335 |

*Primary Examiner*—Harry N. Haroian
*Attorney, Agent, or Firm*—John C. Barnes

[57] ABSTRACT

A surgical drape is disclosed which is combined with suture tapes which are presurgically positioned adjacent the incision such that after surgery and removal of the surgical drape the tapes are approximate the incised skin margin to readily close the incision. The device comprises a pair of spaced sheets coated with a microporous pressure-sensitive adhesive having a liner over the adhesive, at least one of the sheets carries a plurality of spaced fastening tapes opposite the adhesive coated surface for attachment to the other sheet by joining similar tapes on the second sheet. The tapes extend toward the marginal edge of the adjacent sheet and are folded back upon themselves. A surgical drape is then disposed releasably over the tapes and sheets and covers the space between the sheets defining the line for the incision.

2 Claims, 6 Drawing Figures

SURGICAL DRAPE AND SUTURE

BACKGROUND OF THE INVENTION

1. Field of the Invention

This invention relates to a new suturing technique and in one aspect to an improved surgical drape combined with the suturing member such that the sutures will be in approximate position adjacent the marginal edges of the skin prior to its being incised to be in position upon completion of surgery to rematch the sides of the wound.

2. Description of the Prior Art

Sutures have been used for holding surgical wounds together and retention sutures hold the wound together under tension and are usually made of nylon and penetrate the skin at positions spaced widely from the wound. Closure sutures are sewn to the skin margin to bring the marginal edges of the skin into approximation to heal. Outside surface sutures are taken out after the wound has had a chance to mend while buried sutures are used on different layers of the skin tissue and are positioned under the skin. All of these types of sutures penetrated the interior tissue of the body.

Advances in suturing has led to the use of staples which were used to draw the skin together and avoid damage to the inner tissue to the extent caused by placement of the plastic closure sutures. Further advancement led to the pressure-sensitive adhesive tape closures or steristrips and the butterfly sutures which are adhesive strips placed across the wound. These sutures avoided any damage to the interior tissue but were put in place after the operation. Thus, it was necessary to try to rematch the skin on the opposite sides of the wound, which, is not easy if one is trying to proximate, i.e. match the opposed tissue.

Thus, there are disadvantages with all the prior techniques for repairing the surgical wound. Some of these disadvantages are the fact that the inner tissue is damaged due simply to the suturing. The suturing may be handled in such a manner that a foreign body or germ may be injected into the wound or the suture material may serve as a wick. Invasive sutures are also painful. If the skin is moist, tape sutures will not stick well, and it is necessary to utilize some aid to adhesion such as tincture of benzoin as an aid. In the event of an infection in a surgical wound, it is often necessary to remove the sutures such that the wound may be reopened. When closed subsequently, invasive sutures again cause further tissue damage and pain.

The present invention overcomes the disadvantages afforded by prior art suturing techniques. First of all, the skin closures of the present invention are applied prior to making the incision. This is advantageous in that the sutures are in place to proximate the edges of the wound prior to making the incision, and linear approximation is achieved prior to the opening of the skin such that it may be easily matched. The skin is treated for improved adhesion prior to the incision being made such that attempts to apply the suturing material will not be frustrated. The combination of the drape and skin closure or suture dressing affords the rapid closing of the incision after surgery and affords a means whereby the wound may be opened without removing the sutures in the event of some cause to do so. This avoids the necessity of further puncturing the skin to rebind the wound.

Additionally, the sutures may be readjusted for tension after the patient leaves the operating room, postoperatively at will. The sutures are noninvasive such as the steristrips and the butterfly sutures. There is no pain associated with the suturing and they are easily removed in any sequence desired, and need not be seriatim. Because the skin closures are incorporated into the larger drape and are adhered to a large area of the skin, they afford good tension sutures with less irritation to the skin surface due to the shear stress on the adhesive. This feature protects the skin from tears and the patient from discomfort because of the stress on small areas of the skin.

SUMMARY OF THE INVENTION

The present invention thus provides for a combined surgical drape and suture device comprising a sheet of porous nonwoven fibrous material coated with microporous pressure-sensitive adhesive on one surface. The adhesive is covered by a release liner prior to application to the patient. The sheet is formed with a long narrow centrally positioned slot dividing the sheet substantially into two halves and separated sheets except for areas of attachment near opposed marginal edges. On the surface of the halves opposite the adhesive coat are positioned a plurality of fastening tapes. The fastening tapes are secured at one end to the surface of the sheet half opposite the adhesive coating and extend toward the edge of the slot and are then folded back upon themsleves leaving the slot or space between the sheets free of the fastening tapes.

A drape is positioned releasably over the second surface of said sheets and said fastening tapes and over the slot therebetween. The drape is provided with a pressure-sensitive adhesive coating on that surface covering or spanning the slot to adhere to the skin and define the location for the incision.

The present invention thus provides an improvement over other surgical drapes and suturing for skin closing techniques in that the suture material is positioned in place prior to incising the skin, thus the approximating of the skin tissue is made prior to the incision, and the sides of the wound are easily rematched linearly. There is no penetration of the skin, which can act as a wick to draw germs into the wound or cause discomfort, and the closure of the wound with these tension sutures is not frustrated because of dampness of the skin around the incision.

The fastening tapes are preferably plastic coated fine wires which are secured to the halves of the pressure-sensitive adhesive sheet and opposed tapes across the slot are matched by color to permit them to be easily matched and twisted together to close the wound.

DESCRIPTION OF THE ACCOMPANYING DRAWING

The present invention will be more clearly understood after reading the following detailed description which refers to the accompanying drawing wherein.

DETAILED DESCRIPTION OF THE PRESENT INVENTION

Figure 1:
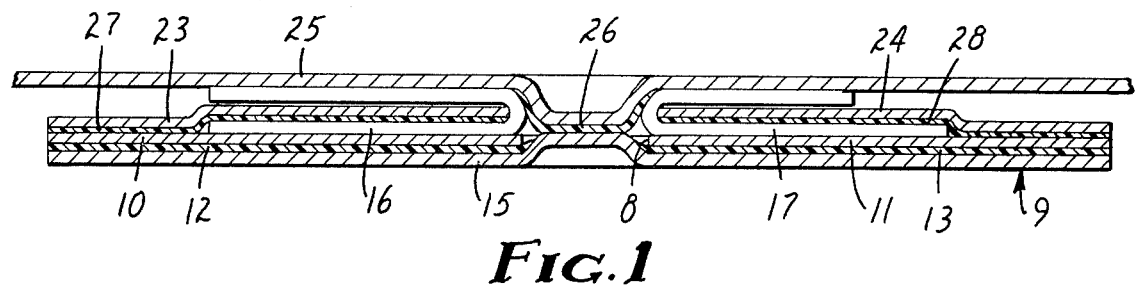
FIG. 1 is a sectional view of the surgical drape and skin closure device.
Figure 2:
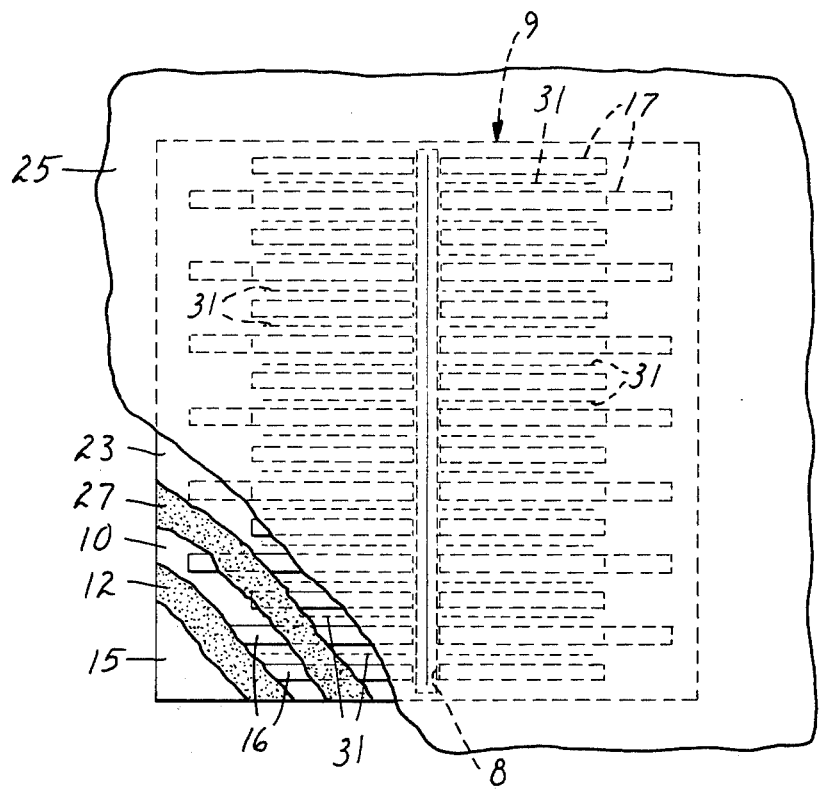
FIG. 2 is a plan view of the drape and skin closure device, with the drape broken away.

Referring now to the FIGS. 1 through 4 it will be seen that the surgical drape and skin closure device of the present invention comprises a sheet 9 of a porous material preferably a unified inextensible nonwoven fibrous fabric on one surface of which is coated a continuous but microporous water-insoluble viscoelastic pressure-sensitive adhesive material 12. The sheet 9 may be formed of a nonwoven fibrous translucent microporous breathable surgical tape as disclosed in U.S. Pat. No. 3,121,021, issued Feb. 11, 1964 to F. S. Copeland.

The sheet 9 has a elongate narrow centrally disposed slot 8 die cut therein and extending to marginal edges of the sheet 9, dividing the sheet substantially into halves or two sheets 10 and 11, separated by the narrow space. The slot 8 has opposed spaced parallel marginal edges. The adhesive coated surface of the sheet 9 is covered by a release liner 15 adapted to autoclave temperatures.

Figure 3:
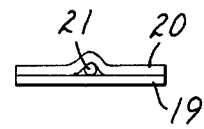
FIG. 3 is a cross-sectional view of a fastening tape.

Adhered to the surface of the halves or sheets 10 and 11 on the surface thereof opposite the adhesive coated surface are a plurality of fastening tapes 16 and 17, respectively. The fastening tapes comprise flexible material capable of being joined together and they have one end thereof secured to the associated sheet with the remainder of the tape extending toward the adjacent marginal edge of the slot 8 and then the tape is folded back upon itself so as not to obstruct the space defined by the slot 8 between the marginal edges of the sheets. The fastening tapes 16 and 17 are preferably polymeric coated strong flexible wires which may twist together easily and remain in the twist-tie relationship. Referring specifically to FIG. 3 there is illustrated in cross section a fastening tape 16 and 17 comprising a first strip of plastic material 19 to which is laminated strip 20 bonding therebetween the length of small diameter wire 21. The surface 19 may be bonded to the surface of the sheet 10 or 11 opposite the adhesive coating or it may be laminated thereto by second sheets 23 and 24 of breathable porous nonwoven fibrous fabric carrying a continuous but microporous pressure-sensitive adhesive coating 27 and 28 which is water-insoluble viscoelastic which is aggressively tacky in its normal dry state, e.g. as disclosed in the Copeland patent and/or available from Minnesota Mining and Manufacturing Company of Saint Paul, Minnesota, under the tradename Micropore surgical tape. The sheets 23 and 24 will thus secure, as by bonding, one end of the tapes to the sheets 10 and 11, respectively, by a laminated structure. The extended ends of the fastening tapes 16 and 17 on each of the sheets 10 and 11 will thus be folded back upon themselves on the surface of the sheets 23 and 24, which are opposite the halves or sheets 10 and 11.

A surgical drape 25 is positioned in laminate fashion over the sheet 9, and thus over the sheets 23 and 24 to span the slot 8. The drape 25 is positioned releasably over the halves or sheets 10 and 11 and is coated with a nonirritating or nonmacerating (nonirritating) adhesive 26 at least on that surface thereof disposed over the slot 8. This adhesive coating 26, as illustrated in the drawing, is thus protected also by the liner 15. The adhesive 26 extends beyond the spacing between the sheets 10 and 11 to lightly adhesively adhere the drape to the sheets 10 and 11 via the tapes 16 and 17 and the sheets 23 and 24.

The fastening tapes on each half of the sheet 9 are disposed in opposed aligned relationship with a similar color of fastening tape on the opposite half or sheet. The tapes are aligned such that when they are joined together the sheets 10 and 11 are retained in their opposed position and one sheet is not moved linearly of the other.

On larger suture devices particularly, the sheet 9 is formed with perforated slits extending perpendicular to the marginal edges of slot 8 into the halves 10 and 11. The slits 31 begin about one-eight inch from the marginal edge and are perforate slits formed for example with one-quarter inch slits joined by one-sixteenth inch lands. As the skin is stretched to open the incision for performing the operative procedures the slits can open by tearing or fracturing of the uncut lands as necessary to allow for stretch along the edges of sheets 10, 11, 23 and 24.

Figure 5:
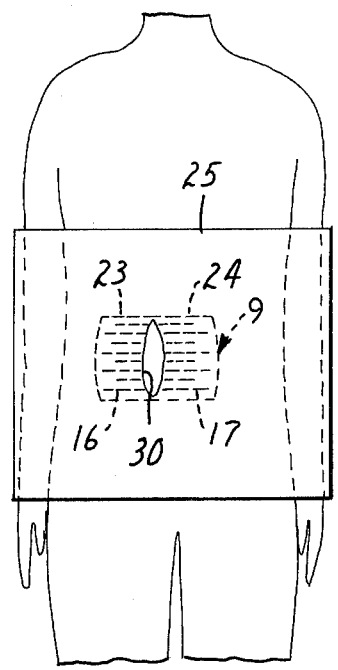
FIG. 5 is a schematic view showing the combined surgical drape and skin closure device on a patient.
Figure 6:
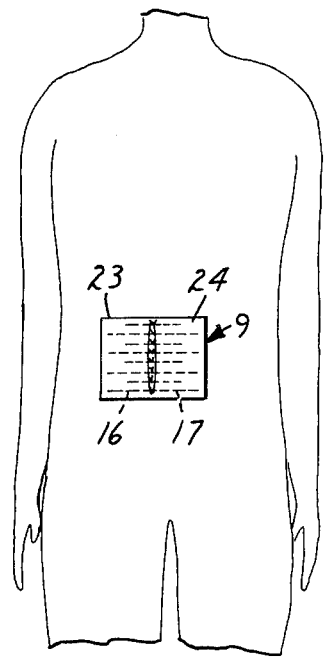
FIG. 6 is a view illustrating the device upon completion of the surgery.
Figure 4:
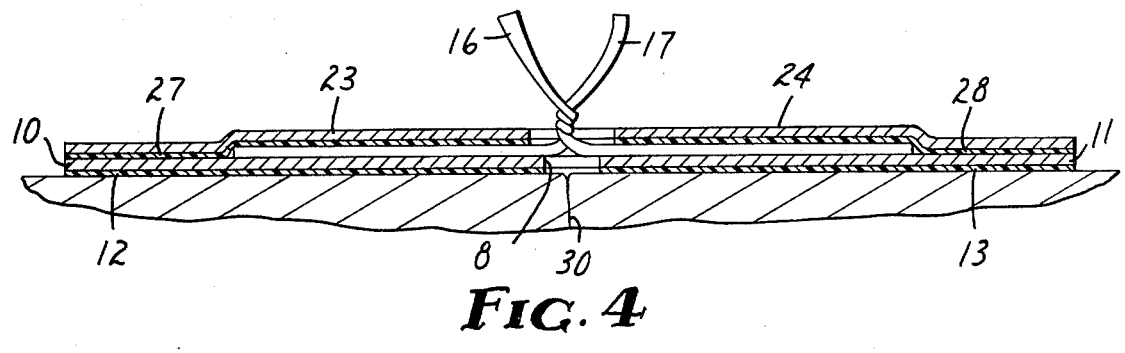
FIG. 4 is a fragmentary plan view of the skin closure device with portions thereof broken away to show interior members.

When preparing the drape for surgery, the liner 15 is removed. The skin closure device is then carefully placed upon the body of the patient with the slot 8 carefully positioned along the line of the required incision. The skin can be prepared by cleansing and treatment to increase adhesion if necessary. With the suture dressing or device in place the drape 25 is unfolded to cover the body as shown in FIG. 5. The drape is adhered to the skin by adhesive 26 being pressed against the skin between the marginal edges of the slot 8. The incision is now made through the drape 25 along a line (if desired) printed on the drape 25 and aligned in the slot. The adhesive 26 protects the sheets 10, 11, 23 and 24 during surgery. The incision, identified by reference numeral 30, can be opened without any substantial disruption of the adhesive bond between the drape 25 and the skin or between the sheets 10 and 11 and the skin.

Upon completion of the surgical manipulations the drape 25 is carefully removed from the patient and released from tapes 16 and 17. The sides of the skin tissue are drawn together and the sheet 10 is joined to the sheet 11 to hold the incision closed by fastening a tape 16 to the sheet 11. In the illustrated embodiment, this is afforded by taking opposed alinged fastening tapes of matched color or length and bringing them together by twisting the tapes together one or more times. The tapes 16 and 17 permit the suture or closure fastening device to be reopened for cleaning or a reopening of the wound to permit drainage if necessary without further damage to the skin tissue.

The suture devices of the present invention may vary in size and can be used for facial surgery or abdominal surgery, requiring, obviously, a larger size. The slot 8 can have a width of one-eight to three-eights inches and the slot will have a length of two inches to twelve inches. The perforated slits 31 may extend back from the marginal edge of the slots one to one and one-half inches.

The suture devices may also be provided with pressure-sensitive adhesive fastening tapes to fasten a half 10 to the half 11, for example. These tapes could be placed in alternate order with the twist tapes, and each tape could be secured at one end to the sheet and the free end folded back with a removable liner covering the free end of the fastening tape beneath the drape 25. These adhesive tapes could aid in mating the proximate edges of the skin vertically as well as linearly.

Having described the present invention with reference to a preferred embodiment, it is to be understood that changes can be made without departing from the invention as defined by the appended claims.

I claim:

1. A suture device comprising a sheet of nonwoven fibrous fabric coated on one surface with nonirritating pressure-sensitive adhesive and having a long narrow centrally disposed slot extending transversely across said sheet to points adjacent opposite side edges thereof, a release liner covering said adhesive and spanning said slot, and porous fibrous adhesive sheets carrying a plurality of spaced fastening tapes adhesively attaching said tapes on the uncoated surface of said fabric on one side of said slot for attachment to similar fastening tapes on the surface of the sheet on the opposite side of the slot, said fastening tapes being secured to said uncoated surface at one end and projecting toward the slot and folded back upon themselves, said fastening tapes comprising lengths of flexible wire material coated with a polymeric coating.

2. A suture device according to claim 1 wherein the fastening tapes on each side of the slot are aligned with a tape on the other side such that upon joining the tapes the opposed marginal edges of said sheet defining said slot are held in opposed aligned relationship.

* * * * *